United States Patent [19]

Horodysky et al.

[11] Patent Number: 4,532,056

[45] Date of Patent: Jul. 30, 1985

[54] LUBRICANT COMPOSITION CONTAINING A BORON REACTION PRODUCT

[75] Inventors: Andrew G. Horodysky, Cherry Hill; Richard S. Herd, Woodbury, both of N.J.

[73] Assignee: Mobil Oil Corporation, New York, N.Y.

[21] Appl. No.: 528,358

[22] Filed: Aug. 31, 1983

[51] Int. Cl.³ ............................................... C10M 1/54
[52] U.S. Cl. .............................. 252/49.6; 252/389 R; 260/462 R; 260/462 C; 564/8
[58] Field of Search ........................ 252/49.6, 389.41; 260/462 R, 462 C; 564/8

[56] References Cited

U.S. PATENT DOCUMENTS

| | | | |
|---|---|---|---|
| 4,195,977 | 4/1980 | Newman | 252/396 |
| 4,303,540 | 12/1981 | Schuster | 252/49.6 |
| 4,389,322 | 6/1983 | Horodysky | 252/49.6 |

*Primary Examiner*—Jacqueline V. Howard
*Attorney, Agent, or Firm*—Alexander J. McKillop; Michael G. Gilman; Van D. Harrison, Jr.

[57] ABSTRACT

Partially borated etherdiamine-acyl sarcosines have been found to be effective multifunctional additives when added to lubricants or liquid fuels. Some of its properties include antirust, antioxidant and friction reducing activities.

31 Claims, No Drawings

LUBRICANT COMPOSITION CONTAINING A BORON REACTION PRODUCT

BACKGROUND OF THE INVENTION

1. Field of the Invention

This invention relates to the inhibition of rust and corrosion in lubricants and fuels. More particularly, the invention relates to lubricants and fuels to which has been added an antirust or anticorrosion amount of a partial borate, partial acyl sarcosine salt of an etherdiamine and to the products per se.

2. Discussion of the Prior Art

It is well known that, under certain conditions, metal parts being lubricated will rust. That is to say, when certain types of materials that are normally susceptible to deterioration by oxidation or by corrosion come into contact with various organic media, rust may form. Organic compositions in both the liquid and solid form can induce such corrosion or oxidation. For example, it is known that liquid hydrocarbons in the form of various fuel oils, such as petroelum distillate hydrocarbon fuels, lubricating oils, or greases therefrom, tend to accumulate considerably quantities of water when maintained for long periods of time in storage vessels; and when subsequently brought into contact with metal surfaces in their functional environments, deterioration of said surfaces as a result of rust and corrosion occurs. In addition, where such lubricating oils are incorporated into lubricants in the form of greases, similar deleterious results are encountered.

No art is known that teaches or suggests the reaction product of the present compositions. It is well known that amines and other nitrogen-containing compounds have been used as antioxidants. For example, N-phenylalpha-naphthylamine has been used alone and in combination with other materials as an antioxidant.

Many varied borated amides, borated alkanolamines, borated ureas, amine salts or boron acids, chlorinated amine-boron complexes and aromatic amine-boron mixtures have been used in the past in commercial lubricant and fuel applications as described in U.S. Pat. Nos. 3,449,362, 3,354,025, 2,999,064, 4,226,734, 3,076,835, 4,025,445, 3,014,870, 3,014,869 and 3,007,873. In fact, alkylamines, alkyldiamines and borated adducts of alkylamines and diamines have been used as friction reducing additives in lubricants as described in U.S. Pat. No. 4,328,113. The partially borated N-hydrocarboxy alkylenediamine-acyl sarcosine salts described here provide advantages in antirust, friction-reducing, oxidative and high temperature stability performance properties unavailable in any of the prior art statements. The additive compositions, as well as the lubricant and fuel compositions made therefrom are believed to be novel, and are not believed to be described in any reference.

SUMMARY OF THE INVENTION

In accordance with the invention, there is provided a lubricant or liquid fuel composition comprising a major proportion of a lubricant or fuel and an antirust, antifriction or anticorrosion amount of a product of reaction obtained by reacting (1) an etherdiamine of the formula

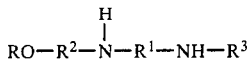

wherein R is a hydrocarbyl group containing 6 to 20 carbon atoms, $R^1$ and $R^2$ are $C_2$ to $C_3$ alkylene groups and $R^3$ is hydrogen or a hydrocarbyl group having 1 to 6 carbon atoms, with (2) a boron-containing compound and (3) an acyl sarcosine of the formula:

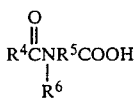

where $R^4$ is a hydrocarbyl group containing 6 to 20 carbon atoms $R^5$ is a hydrocarbylene group containing 1 to 6 carbon atoms and $R^6$ is hydrogen or a $C_1$ to $C_6$ hydrocarbyl group. "Hydrocarbyl" (as used per se and in "hydrocarboxy", e.g.) includes alkyl, alkenyl, cycloalkyl, cycloalkenyl, alkayl, arylalkyl, and the like, and mixtures of these. "Hydrocarbylene" includes those members between two nitrogen atoms or between a nitrogen and a carbon atom, e.g., alkylene and alkenylene groups.

In addition, the invention provides the product of reaction.

DESCRIPTION OF SPECIFIC EMBODIMENTS

Partially borated N-hydrocarboxy hydrocarbylenediamine-acyl sarcosine salts demonstrate exceptional anti-rust and friction reducing properties when formulated into lubricants at low additive concentrations. These partially borated N-hydrocarboxyalkylene hydrocarbylenediamine-acyl sarcosine salts can be synthesized by the partial boration of etherdiamines followed by reaction with and salt formation by the appropriate acyl sarcosine.

Some of the useful diamines include hexoxypropyl-1-3-propylene-diamine, heptoxypropyl-1,3-propylenediamine, oleoxypropyl-1,3-propylene-diamine, oxtoxypropyl-1,3-propylenediamine, nonoxypropyl-1,3-propylene-diamine, decoxypropyl-1,3-propylenediamine, dodecoxypropyl-1,3-propylene-diamine, tetramethylnonoxypropyl-1,3-propylenediamine and mixtures of two or more of these. All the R groups mentioned are alkyl. Others can be an alkenyl group, an aryl group, an alkaryl group, an aralkyl group or a cycloalkyl group. The aryl portion will contain 6 to 14 carbon atoms.

The boron compound can be any capable of boration. Preferred are boron oxide, the metaborates and a boron compound of the formula:

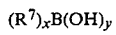

wherein $R^7$ is a $C_1$ to $C_6$ alkyl group, x is 0 to 3 and y is 0 to 3, the sum of x and y being 3. Included within the formula are boric acid and alkyl borates, such as the mono-, di- and trimethyl borates, the mono-, di- and triethyl borates, the mono-, di- and tribuyty borates and the mono-, di- and trihexyl borates.

The acyl sarcosines useful in practicing the invention include lauroyl sarcosine, oleoyl sarcosine, soyoyl sarcosine, tallowoyl sarcosine, hydrogenated tallowoyl sarcosine, linoleoyl sarcosine, cocoyl sarcosine and decoyl sarcosine, and mixtures thereof.

In carrying out the reaction, we preferably first react the boron compound with the diamine such that at least about 5% and up to 95% of the available amino groups are reacted and then from about 5% to about 100% of the remaining amino groups are reacted with the acyl sarcosine. In this case, an excess of sarcosine may be used if all remaining amino groups are reacted.

The order of reaction just given is not believed to be critical, and the diamine may be reacted first with the acyl sarcosine so that about 5% to about 95% of the amino groups react therewith, followed by reaction of from about 5% to 100% of the remaining amino groups with boron compound. An excess of boron compound is preferred if all remaining amino groups are to be borated.

The reaction of diamine with the boron compound may be carried out at from about 80° C. to about 260° C., preferably from about 120° C. to 180° C. Reaction of the remaining amino groups with sarcosine can take place at from about 20° C. to about 130° C., preferably 50° C. to 90° C. If the sarcosine—amine reaction were carried out first at this latter temperature (20° C. to 130° C.), it is contemplated that boration could take place at from about 80° C. to about 150° C., preferably about 100° C. to 120° C., to minimize amide formation and to maximize the amounts of borated diamine—acyl sarcosine salt formation.

Times of reaction are not critical. Thus, although we do not wish to be confined to any time limitation, we contemplate that the products of this invention can be made by carrying out the reaction for from 1 to 20 hours.

Solvents are preferred in carrying out the invention. Broadly, any solvent can be used that does not react, is a solvent for both the reactants and the reaction product and can be removed easily or is compatible with the environment in which the product will be used. We prefer the hydrocarbon solvents such as toluene, benzene, xylenes for either reaction. Low molecular weight alcohols such as butanol or hexamethylene glycol can be used for the boration reaction addition or in place of hydrocarbon solvents.

The borated compounds disclosed herein are used with lubricating oils to the extent of from about 0.1% to about 10% by weight of the total composition. Furthermore, other additives, such as detergents, antioxidants, antiwear agents, viscosity index improvers, pour depressants, dispersants, and the like may be present. These can include phenates, sulfonates, succinimides, metallic zinc or ashless dithiophosphates, phosphorothionyl disulfides, phosphites, sulfides, polymers, calcium and magnesium salts and the like.

An important feature of the invention is the ability of the additive to improve the resistance to oxidation of oleaginous materials such as lubricating oils, either a mineral oil or a synthetic oil, or mixtures thereof, or a grease in which any of the aforementioned oils are employed as a vehicle. In general, mineral oils, both paraffinic, naphthenic and mixtures thereof, employed as a lubricating oil or as the grease vehicle, may be of any suitable lubricating viscosity range, as for example, for about 45 SSR at 100° F. to about 6000 SSU at 100° F., and preferably from about 50 to about 250 SSR at 210° F. These oils may have viscosity indexes ranging to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, including calcium or lithium soaps which include calcium or lithium stearates or calcium or lithium hydroxystearates. These are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing the aforementioned improved grease in accordance with the present invention.

If synthetic oils are preferred as lubricants, either per se or as a grease vehicle, various synthetic oils may be successfully utilized. Typical synthetic vehicles include polyisobutylenes, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted bis(p-phenoxy phenyl)ether, phenoxy phenylethers.

It is to be understood that the compositions contemplated herein may also contain other materials. For example, other corrosion inhibitors, extreme pressure agents, viscosity index improvers, coantioxidants, antiwear agents and the like can be used. These include, but are not limited to, phenates, sulfonates, succinimides, zinc dialkyl dithiophosphates, and the like. These materials do not detract from the value of the compositions of this invention; rather the materials serve to impart their customary properties to the particular compositions in which they are incorporated.

Mineral oil heat exchange fluids particularly contemplated in accordance with the present invention have the following characteristics: high thermal stability, high initial boiling point, low viscosity, high heat-carrying ability and low corrosion tendency.

Further, the transmission fluids of consequence to the present invention are blends of highly refined petroleum base oils combined with VI improvers, detergents, defoamants and special additives to provide controlled-friction or lubricity characteristics. Varied transmission design concepts have led to the need for fluids with markedly different frictional characteristics, so that a single fluid cannot satisfy all requirements. The fluids intended for use in passenger car and light-duty truck automatic transmissions are defined in the ASTM Research Report D-2; RR 1005 on "Automatic Transmission Fluid/Power Transmission Fluid Property and Performance Definitions. Specifications for low-temperature and aircraft fluids are defined in U.S. Government Specification MIL-H-5606A.

In addition, the oxidation and corrosion resistance of functional fluids such as hydraulic fluids can be improved by the adducts of the present invention.

The products of this invention can also be employed in liquid hydrocarbon fuels, alcohol fuels or mixtures thereof, including mixtures of hydrocarbons, mixtures of alcohols and mixtures of hydrocarbon and alcohol fuels. About 25 pounds of about 500 pounds or preferably about 50 to 100 pounds of borated etherdiamine sarcosine per thousand barrels of fuel for internal combustion engines may be used. Liquid hydrocarbon fuels include gasoline, fuel oils and diesel oils. Methyl and ethyl alcohols are examples of alcohol fuels.

In general, the reaction products of the present invention may be employed in a lubricant in any amount which is effective for imparting the desired degree of antirust activity, antioxidant or friction reduction activity. In these applications, the product may be effectively employed in amounts from about 0.1% to about 10% by weight, and preferably from about 1% to about 5% of the total weight of the composition.

The following Examples will illustrate the invention. It will be understood that they are illustrative only and it is not intended that the invention shall be limited thereto.

EXAMPLE 1

Partially Borated N-Tetramethylnonyloxypropyl-1,3-propylenediamine

N-Tetramethylnonyloxypropyl-1,3-propylenediamine (commercially available as Duomeen EA-13 from Armak Co. and derived from an isomeric tridecyl alcohol consisting primarily of tetramethylnonyl alcohol) had an average molecular weight of approximately 315. Approximately 255 g of this diamine, about 100 g of toluene and 9 g of boric acid were charged to a reactor fitted with an agitator, heater, and Dean-Stark tube with condenser. The reactor contents were heated up to about 155° C. with agitation using a slow nitrogen purge of the vapor space. The reactor contents were held at about 155° C. for four additional hours until water evolution via azeotropic distillation ceased. The solvent was removed by vacuum distillation at 150° C. and the partially borated ether diamine was filtered hot through diatomaceous earth.

EXAMPLE 2

Partially Borated Ether Diamine-Partial Lauroyl Sarcosine Salt

Approximately 32 g of the partially borated N-tetramethylnonyloxypropyl-1,3-propylenediamine prepared in Example 1 and 7 g of lauroyl sarcosine were reacted with agitation for about ½ hour at approximately 60° C. The product was an amber colored fluid at 60° C.

EXAMPLE 3

Partially Borated Ether Diamine-Partial Lauroyl Sarcosine Salt

Approximately 32 g of the partially borated ether diamine prepared in Example 1 and 14 g of lauroyl sarcosine were reacted with agitation for ½ hour at approximately 60° C. The product was an amber colored fluid at 60° C.

EXAMPLE 4

Partially Borated Ether Diamine-Partial Oleoyl Sarcosine Salt

Approximately 32 g of the partially borated ether diamine prepared in Example 1 and 9 g of oleoyl sarcosine were reacted with agitation for about ½ hour at approximately 60° C. The product was an amber colored fluid at reaction temperatures.

EXAMPLE 5

Partially Borated Ether Diamine-Partial Oleoyl Sarcosine Salt

Approximately 32 g of the partially borated ether diamine prepared in Example 1 and 18 g of oleoyl sarcosine were reacted with agitation for ½ hour at approximately 60° C. The product was an amber colored fluid at reaction temperatures.

EXAMPLE 6

Partially Borated Ether Diamine-Partial Cocoyl Sarcosine Salt

Approximately 32 g of the partially borated ether diamine prepared in Example 1 and 7 g of cocoyl sarcosine were reacted with agitation for about ½ hour at approximately 60° C. The product was an amber colored fluid at reaction temperatures.

EXAMPLE 8

Borated N-Tetramethylnonyloxypropyl-1,3-propylenediamine

Approximately 324.5 g of N-tetramethylnonyloxypropyl-1,3-propylenediamine similar to that described in Example 1, about 100 g of toluene and about 23 g of boric acid were charged to a 1 reactor fitted with an agitator, heater and Dean-Stark tube with condenser. The reactor contents were heated up to about 155° C. with agitation using a slow nitrogen purge of the vapor space. The reactor contents were held at about 155° C. until water evolution via azeotropic distillation ceased. The solvent was removed by vacuum distillation and the borated ether diamine was filtered hot through diatomaceous earth.

EXAMPLE 9

Partially Borated Ether Diamine-Partial Lauroyl Sarcosine Salt

Approximately 32 g of the partially borated ether diamine prepared about in Example 8 and 3.5 g of lauroyl sarcosine were reacted with agitation for about ¾ hour at 55°-60° C. The product was an amber colored fluid at reaction temperatures.

Example 10

Partially Borated Ether Diamine-Partial Lauroyl Sarcosine Salt

Approximately 32 g of the partially borated ether diamine prepared in Example 8 and 7 g of lauroyl sarcosine were reacted with agitation for about ¾ hour at 55°-60° C. The product was an amber colored fluid at reaction temperatures.

EXAMPLE 11

Partially Borated Ether Diamine-Partial Lauroyl Sarconsine Salt

Approximately 32 g of partially borated ether diamine prepared as described in Example 8 and 14 g of lauroyl sarcosine were reacted with agitation for about ¾ hour at 55°–60° C. The product was an amber colored fluid at reaction temperatures.

EXAMPLE 12

Partially Borated Ether Diamine-Partial Oleoyl Sarcosine Salt

Approximately 32 g of the partially borated ether diamine prepared in Example 8 and 9 g of oleoyl sarcosine were reacted with agitation for about ¾ hour at 55°–60° C. The product was an amber colored fluid at reaction temperatures.

EXAMPLE 13

Partially Borated Ether Diamine-Partial Cocoyl Sarcosine Salt

Approximately 32 g of the partially borated ether diamine prepared in Example 8 and 7 g of cocoyl sarcosine were reacted with agitation for about ¾ hour at 55°–60° C. The product was an amber colored fluid at reaction temperatures.

The products of the examples described above were added at the 2 wt. % level to a fully formulated lithium hydroxystearate soap grease without any other added antirust additive. The fully formulated grease contained zinc dithiophosphates derived from alkanols. The grease was then evaluted for antirust properties using an extremely severe rust test performed with 5% synthetic sea water.

A standard test method (modified ASTM D1743) for corrosion preventive properties of lubricating grease was used. The method covers the determination of the corrosion preventive properties of greases using grease-lubricated tapered roller bearings stored under wet conditions. After cleaning, the bearing cup raceways are examined for evidence of corrosion.

TABLE 1

Evaluation of Antirust Properties

| Composition Tested | Concentration of Additive, Wt. % | Rust Test Results* |
| --- | --- | --- |
| Base Grease** | — | 3–10%, 3–15% |
| Example 2 plus grease | 2 | 1, 1 |
|  | 2 | 1, 2 |
| Example 3 plus grease | 2 | 1, 2+ |
|  | 2 | 1, 2+ |
| Example 4 plus grease | 2 | 3–5%, 3–5% |
| Example 5 plus grease | 2 | 1, 3 = 5% |
| Example 6 plus grease | 2 | 2+, 3–2% |
| Example 7 plus grease | 2 | 1, 2+ |
|  | 2 | 2, 2+ |
| Example 9 plus grease | 2 | 2+, 3–1% |
| Example 10 plus grease | 2 | 2+, 2+ |
| Example 11 plus grease | 2 | 1, 2+ |
| Example 12 plus grease | 2 | 2, 2+ |
| Example 13 plus grease | 2 | 2, 2+ |

*A bearing cup raceway showing no corrosion is rated 1. No more than 3 spots of a size just sufficient to be visible to the naked eye is rated 2. More than 3 spots, but less than 1% of the surface area is rated 2+. 1% or more of the surface area corroded is rated 3. (Note: the approximate percent of surface area corrosion is shown with a 3 rating.)
**The base for the grease was a mixture of solvent paraffinic and solvent naphthenic mineral oils The antirust test results clearly show the exceptional antirust properties provided by the partially borated N-hydrocarbyloxy hydrocarbyldiamine-partial acyl sarcosine salts.

We claim:

1. A product of reaction made by reacting (1) a diamine of the formula

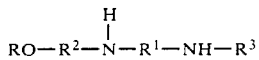

wherein R is a hydrocarbyl group containing 6 to 20 carbon atoms, $R^1$ and $R^2$ are $C_2$ or $C_3$ hydrocarbylene groups, preferably alkylene groups and $R^3$ is hydrogen or a hydrocarbyl group having 1 to 6 carbon atoms, with (2) a boron-containing compound and (3) an acyl sarcosine of the formula:

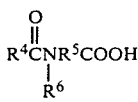

where $R^4$ is a hydrocarbyl group containing 6 to 20 carbon atoms, $R^5$ is a hydrocarbylene group containing 1 to 6 carbon atoms and $R^6$ is hydrogen or a $C_1$ to $C_6$ hydrocarbyl group, the reactions being carried out at a temperature within the range of from about 80° C. to about 260° C., such that in the initial reaction from about 5% to about 95% of the amino groups are reacted and in the final reaction from about 5% to about 100% of the remaining amino groups are reacted.

2. The product of claim 1 wherein hydrocarbyl is alkyl, alkenyl, aryl, aralkyl, alkaryl, cycloalkyl, cycloalkenyl or mixtures thereof.

3. The product of claim 1 wherein hydrocarbylene is alkylene or alkenylene.

4. The product of claim 1 wherein the diamine is hexoxypropyl-1,3-propylenediamine, heptoxypropyl-1,3-propylenediamine, oleoxypropyl-1,3-propylenediamine, decoxypropyl-1,3-propylenediamine, dodecoxypropyl-1,3-propylenediamine, tetramethylnonoxypropyl-1,3-propylenediamine or mixtures thereof.

5. The product of claim 1 wherein the sarcosine is lauroyl sarcosine, oleoyl sarcosine, soyoyl sarcosine, tallowoyl sarcosine, hydrogenated tallowoyl sarcosine, linoleoyl sarcosine, cocoyl sarcosine or decoyl sarcosine, and mixtures thereof.

6. The product of claim 1 wherein the diamine is first reacted with the boron compound at from about 80° C. to about 260° C. to react from about 5% to about 95% of the amino group therewith, followed by reaction of from about 5% to about 100% of the remaining amino groups with the acyl sarcosine at from about 20° C. to about 130° C.

7. The product of claim 1 wherein the diamine is first reacted with the acyl sarcosine at fom about 20° C. to about 130° C. to react from about 5% to about 95% of the amino groups therewith, followed by reaction of from about 5% to about 100% of the remaining amino groups with the boron compound at from about 80° C. to about 150° C.

8. The product of claim 6 wherein the diamine is N-tetramethylnonyloxypropyl-1,3-propylenediamine, the boron compound is boric acid and the sarcosine is lauroyl sarcosine.

9. The product of claim 6 wherein the diamine is N-tetramethylnonyloxypropyl-1,3-propylenediamine, the boron compound is boric acid and the sarcosine is oleoyl sarcosine.

10. The product of claim 6 wherein the diamine is N-tetramethylnonyloxypropyl-1,3-propylenediamine, the boron compound is boric acid and the sarcosine is cocoyl sarcosine.

11. The product of claim 1 wherein the boron compound is boric oxide or is of the formula $$(R^7O)_xB(OH)_y$$

wherein $R^7$ is a $C_1$ to $C_6$ alkyl group, x is 0 to 3, Y is 0 to 3, the sum of x and y being 3.

12. The product of claim 11 wherein the boron compound is boric acid.

13. A lubricant composition comprising a major proportion of a lubricating oil or grease therefrom and an antifriction amount of a product of reaction made by reacting (1) a diamine of the formula $$RO-R^2-\underset{\underset{H}{|}}{N}-R^1-NH-R^3$$

wherein R is a hydrocarbyl group containing 6 to 20 carbon atoms, $R^1$ and $R^2$ are $C_2$ or $C_3$ hydrocarbylene groups, preferably alkylene groups and $R^3$ is hydrogen or a hydrocarbyl group having 1 to 6 carbon atoms, with (2) a boron-containing compound and (3) an acyl sarcosine of the formula:

$$R^4\underset{\underset{R^6}{|}}{\overset{\overset{O}{\|}}{C}NR^5}COOH$$

where $R^4$ is a hydrocarbyl group containing 6 to 20 carbon atoms, $R^5$ is a hydrocarbylene group containing 1 to 6 carbon atoms and $R^6$ is hydrogen or a $C_1$ to $C_6$ hydrocarbyl group, the reactions being carried out at a temperature within the range of from about 80° C. to about 260° C., such that in the initial reaction from about 5% to about 95% of the amino groups are reacted and in the final reaction from about 5% to about 100% of the remaining amino groups are reacted.

14. The composition of claim 13 wherein the diamine is first reacted with the boron compound at from about 80° C. to about 260° C. to react from about 5% to about 95% of the amino group therewith, followed by reaction of from about 5% to about 100% of the remaining amino groups with the acyl sarcosine at from about 20° C. to about 130° C.

15. The composition of claim 13 wherein the diamine is first reacted with the acyl sarcosine at fom about 20° C. to about 130° C. to react from about 5% to about 95% of the amino groups therewith, followed by reaction of from about 5% to about 100% of the remaining amino groups with the boron compound at from about 80° C. to about 150° C.

16. The composition of claim 13 wherein in the compound hydrocarbyl is alkyl, alkenyl, aryl, aralkyl, alkaryl, cycloalkyl, cycloalkenyl or mixtures thereof.

17. The compositions of claim 13 wherein in the compound hydrocarbylene is alkylene or alkenylene.

18. The composition of claim 11 wherein the diamine is hexoxypropyl-1,3-propylenediamine, heptoxypropyl-1,3-propylenediamine oleoxypropyl-1,3-propylenediamine, decoxypropyl-1,3-propylenediamine, dodecoxypropyl-1,3-propylenediamine, tetramethylnonoxypropyl-1,3-propylenediamine or mixtures thereof.

19. The composition of claim 13 wherein in the compound the sarcosine is lauroyl sarcosine, oleoyl sarcosine, soyoyl sarcosine, tallowoyl sarcosine, hydrogenated tallowoyl sarcosine, linoleoyl sarcosine, cocoyl sarcosine or decoyl sarcosine, and mixtures thereof.

20. The composition of claim 14 wherein in the compound the diamine is N-tetramethylnonyloxypropyl-1,3-propylenediamine, the boron compound is boric acid and the sarcosine is lauroyl sarcosine.

21. The composition of claim 14 wherein in the compound the diamine is N-tetramethylnonyloxypropyl-1,3-propylenediamine, the boron compound is boric acid and the sarcosine is oleoyl sarcosine.

22. The composition of claim 14 wherein in the compound the diamine is N-tetramethylnonyloxypropyl-1,3-propylenediamine, the boron compound is boric acid and the sarcosine is cocoyl sarcosine.

23. The composition of claim 13 wherein in the compound the boron compound is boric oxide or is of the formula $$(R^7O)_xB(OH)_y$$

wherein $R^7$ is a $C_1$ to $C_6$ alkyl group, x is 0 to 3, Y is 0 to 3, the sum of x and y being 3.

24. The composition of claim 23 wherein in the compound the boron compound is boric acid.

25. The composition of claim 13 wherein the lubricant is (1) a mineral oil (2) a synthetic oil or a mixture of synthetic oils, (3) a mixture of (1) and (2) or (4) a grease from (1), (2) or (3).

26. The composition of claim 25 wherein the lubricant is a grease of (4).

27. The composition of claim 26 wherein the grease is thickened with a lithium or calcium stearate or a lithium or calcium hydroxystearate.

28. The composition of claim 26 wherein the grease vehicle is a mineral oil.

29. The composition of claim 28 wherein the mineral oil is a mixture of paraffinic and naphthenic fractions.

30. The composition of claim 26 wherein the grease vehicle is a mineral oil and the thickener is lithium hydroxystearate.

31. The composition of claim 19 wherein the thickener is lithium hydroxystearate.

* * * * *